United States Patent [19]

Chang

[11] Patent Number: 5,126,505
[45] Date of Patent: Jun. 30, 1992

[54] KA OIL RECOVERY

[75] Inventor: Te Chang, West Chester, Pa.

[73] Assignee: Arco Chemical Technology, L.P., Wilmington, Del.

[21] Appl. No.: 600,032

[22] Filed: Oct. 18, 1990

[51] Int. Cl.⁵ ............................................. C07D 31/02
[52] U.S. Cl. ................................... 549/529; 549/541
[58] Field of Search ............... 568/361, 576; 549/529, 549/541

[56] References Cited

U.S. PATENT DOCUMENTS

| 3,849,451 | 11/1974 | Stein et al. | 549/541 |
| 3,881,996 | 5/1975 | Schmidt | 549/541 |
| 3,909,366 | 9/1975 | Schmidt et al. | 549/541 |
| 3,949,004 | 4/1976 | Sorgenti et al. | 568/570 |
| 3,983,143 | 9/1976 | Sheng et al. | 549/529 |
| 4,080,387 | 3/1978 | Jubin et al. | 568/570 |
| 4,140,588 | 2/1979 | Schmidt | 549/541 |
| 4,328,372 | 5/1982 | Wu | 568/361 |

Primary Examiner—James H. Reamer
Attorney, Agent, or Firm—William C. Long

[57] ABSTRACT

The invention relates to improved recovery of cycloalkanol/cycloalkanone from epoxidation mixtures which result from olefin epoxidation with cycloalkyl hydroperoxide by hydrolysis of ketal compounds contained in the mixtures.

3 Claims, 1 Drawing Sheet

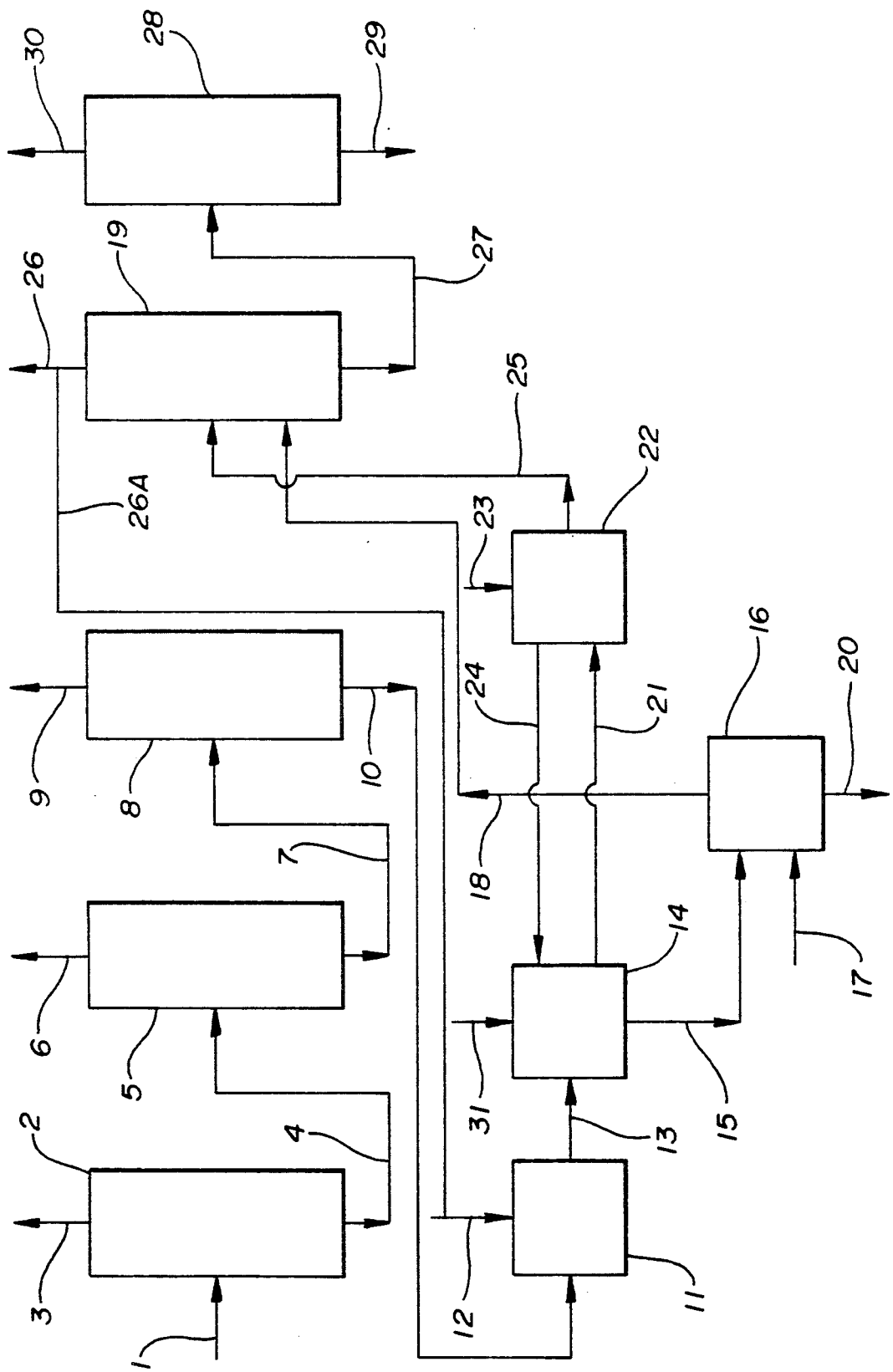

KA OIL RECOVERY

BACKGROUND OF THE INVENTION

1. Field of the Invention

The present invention relates to the recovery of cycloalkanol/cycloalkanone co-products from the epoxidation mixtures which result from the reaction of olefinically unsaturated compounds such as propylene with cycloalkane oxidate comprised of cycloalkyl hydroperoxide. In particular, the invention relates to improved cycloalkanol/cycloalkanone recovery by hydrolysis of ketal compounds which are formed during the epoxidation and/or separation procedures.

2. Description of the Prior Art

The oxidation of cyclohexane to form products including cyclohexyl hydroperoxide (CHHP) is a known reaction.

U.S. Pat. No. 3,927,115 shows the oxidation of cyclohexane with molecular oxygen to form CHHP, cyclohexanol and cyclohexanone, the improvement being carrying out the oxidation in the presence of an alkane having a tertiary carbon, e.g. isobutane.

U.S. Pat. No(s). 3,949,003 and 3,987,115 show the oxidation of cyclohexane in the presence of a tertiary alcohol and a tertiary hydroperoxide to produce OHHP, cyclohexanol and cyclohexanone.

U.S. Pat. No. 3,949,004 shows oxidation of cyclohexane in the presence of a stabilizing agent such as water or tertiary butyl alcohol to produce CHHP, cyclohexanol and cyclohexanone.

U.S. Pat. No. 4,080,387 relates to oxidation of cyclohexane to a product mixture comprised of CHHP, cyclohexanol and cyclohexanone and to the concentration of OHHP by distillation procedures.

U.S. Pat. No. 2,675,407 describes the oxidation of a cylcloalkane dissolved in tertiary butyl alcohol.

U.S. Pat. No. 2,851,496 describes the oxidation of cyclohexane including reacting the product mixture in the presence of a peroxide decomposition catalyst to reduce the CHHP content.

U.S. Pat. No. 3,365,490 relates to the production of adipic acid by oxidizing cyclohexane, separating the reaction mixture with recycle of unreacted cyclohexane and subsequent nitric acid oxidation of the cyclohexanol and cyclohexanone to form adipic acid.

U.S. Pat. No. 3,365,490 relates to the oxidation of cycloalkanes to hydroperoxides and includes a basic treatment of recycle cycloalkane.

U.S. Pat. No. 3,694,511 describes the hydrogenation of cycloalkane by peroxides under conditions effective to preserve catalyst life and activity.

U.S. Pat. No. 3,719,706 separates by-products from cyclohexyl hydroperoxide by water washing.

U.S. Pat. No. 3,923,895 treats the hydroperoxide-containing solution in cycloalkane by heating in the presence of a chromium catalyst in order to obtain cyclohexanone and cyclohexanol.

U.S. Pat. No. 3,927,108 is also concerned with the hydrogenation of cyclohexyl hydroperoxide in the presence of a particular catalyst.

U.S. Pat. No. 3,957,876 describes preparation of CHHP by oxidation of cyclohexane containing a cobalt catalyst in a specially zoned oxidation reactor.

U.S. Pat. No. 4,326,084 shows oxidation of cyclohexane to produce a mixture containing CHHP and decomposing this latter material with a particular, designated catalyst.

U.S. Pat. No. 4,341,907 describes oxidation of cyclohexane in the presence of a particular heavy metal compound catalyst.

U.S. Pat. No. 4,465,861 describes decomposition of a reaction mixture containing CHHP using a specified catalyst combination.

U.S. Pat. No. 4,482,746 likewise shows decomposition of CHHP using a special catalyst combination of components.

U.S. Pat. No. 4,499,305 similarly describes decomposition of CHHP using a special catalyst.

U.S. Pat. No. 4,503,257 decomposes CHHP by using a catalyst consisting of a certain metal on a solid support.

U.S. Pat. No. 4,720,592 describes extracting a cyclohexane oxidation mixture with water followed by hydrogenation to convert the CHHP.

U.S. Pat. No. 3,917,708 describes the oxidation of cyclohexane using a heavy metal salt catalyst.

U.S. Pat. No. 4,163,027 describes a process for working up cyclohexane oxidation mixture by treatment with alkaline metal compound-containing solutions.

U.S. Pat. No. 4,543,427 shows decomposition of CHHP with a supported cobalt catalyst.

U.S. Pat. No. 4,704,476 describes working up a cyclohexane oxidation mixture with aqueous alkali solution.

U.S. Pat. No. 4,814,511 shows working up cyclohexane oxidation mixtures by reaction with cyclo-olefins in the presence of certain, designated catalysts with ultimate hydrogenation of the resulting oxide to the cycloalkanol.

CHHP has been suggested as a reactant for the catalytic epoxidation of olefinically unsaturated compounds such as propylene to form the corresponding oxirane compound. See for example, U.S. Pat. No(s). 3,983,143 and 3,870,729 as well as European Patent 0 129 814.

In such procedures, the co-product derived from the cycloalkane is a cycloalkanone/cycloalkanol (KA Oil) mixture which itself has considerable value. For example, such mixtures are readily converted to the corresponding dibasic acid, e.g. adipic acid, by well-known oxidation procedures.

An important consideration in these technologies has been the recovery of maximum amounts of KA Oil components since these materials are important and valuable co-products.

BRIEF DESCRIPTION OF THE INVENTION

It has now been found that when cycloalkyl hydroperoxide, especially in mixtures from cycloalkane oxidation, is used in the epoxidation of olefinic compounds, during the epoxidation and/or recovery procedures, undesirable ketal by-products are formed through reaction of cycloalkanone with a glycol derivative of the oxirane product. These ketal by-products are difficult to separate from co-product KA Oil and represent a substantial yield loss of the valuable KA Oil as well as the glycol.

In accordance with this invention, the ketal-containing KA Oil mixture is subjected to an hydrolysis reaction under conditions effective to convert the ketal impurity to cycloalkanone and glycol. A KA Oil mixture containing enhanced yields of cycloalkanne can then readily be recovered.

DESCRIPTION OF THE DRAWING

The accompanying drawing illustrates in schematic form practice of the invention.

DETAILED DESCRIPTION

Mixtures treated in accordance with the invention are derived from cycloalkanes having 5 to 12 carbon atoms. cyclohexane is the most useful; examples of other cycloalkanes are cyclopentane, cyclo-octane and cyclododecane.

Methods which are generally known are employed to oxidize the cycloalkane to a cycloalkyl hydroperoxide-containing mixture as illustrated by the art cited above.

The cycloalkane is oxidized by contact with a molecular oxygen-containing gas at reaction conditions to form oxidation products including the cycloalkyl hydroperoxide, cycloalkanol and cycloalkanone. The oxidation conditions are generally well known as evidenced by the prior art recited above. Temperatures ranging from about 80 to 200° C. are usually employed, and reaction pressures are sufficient to maintain cycloalkane in the liquid phase. Preferred temperatures are 130 to 170° C., and especially preferred temperatures are 145 to 155° C. Pressures from atmospheric to 300 psi or higher can be employed, pressures of 100 to 250 psi being preferred.

Various stabilizers and other additives used in the prior art to enhance hydroperoxide formation can be employed.

The molecular oxygen oxidant gas can comprise pure oxygen, but is preferably oxygen admixed with one or more inert gases. Air is especially preferred.

In a particularly preferred practice, the cycloalkane oxidation is carried out in the presence of a stabilizing agent, especially t-butyl alcohol, as described in U.S. Pat. No. 3,949,004, the disclosure of which is incorporated herein by reference. The oxidation mixture can be concentrated as described in U.S. Pat. No. 4,080,387.

Catalytic epoxidation of an olefinically unsaturated compound with the cycloalkyl hydroperoxide is also a known reaction. U.S. Pat. No. 3,983,143 illustrates a particularly preferred method for carrying out this reaction.

In especially preferred practice, propylene is converted to propylene oxide. The invention is not limited to propylene conversion, however; olefinic materials generally can be reacted. The invention is most advantageously applied to mixtures from the epoxidation of $C_2$ to $C_{20}$ alpha olefins.

The epoxidation reaction mixture is conveniently separated by procedures such as those described in U.S. Pat. No(s). 3,881,996, 3,843,488, 3,909,366 and 4,140,588. A KA-Oil mixture comprised of the cycloalkanol and cycloalkanone formed during cycloalkane oxidation as well as by cycloalkyl hydroperoxide conversion during epoxidation is separated and it is this mixture which is treated in accordance with the present invention. It has been found that these mixtures contain, in addition to cycloalkanone and cycloalkanol, quantities of ketal formed by reaction between cycloalkanone and small amounts of glycol which are formed during the epoxidation and/or separation.

According to the invention, the ketal-containing KA Oil mixture is hydrolyzes at conditions effective to convert the ketal impurity to cycloalkanone plus glycol. Appropriate reaction conditions include modestly elevated temperatures, preferably 50 to 150° C. Sufficient water is incorporated with the KA Oil mixture to at least saturate the organic liquid phase.

The hydrolysis should be carried out under acidic conditions in order that the ketal conversion approach equilibrium. Generally, the KA-Oil mixture from the epoxidation has sufficient acidity to carry out the hydrolysis. Mineral acids can be added but are not seen to provide any special advantage and in fact may tend to catalyze unwanted reactions.

From the hydrolysis reaction there is separated a KA Oil stream substantially reduced in ketal impurity content and comprised of significantly enhanced amounts of cycloalkanone.

In preferred practice, the KA-Oil stream from the ketal hydrolysis is subjected to treatment with aqueous caustic in order to hydrolyze esters, especially cycloalkanol esters, thereby further improving KA-Oil yields. The acidic ketal hydrolysis step should precede the caustic treatment, and the caustic treatment has the additional advantage of stabilizing the cycloalkanone and glycol formed during the acidic ketal hydrolysis.

Preferably, the caustic treated KA-Oil stream is washed with water and then subjected to various separation and recycle steps as will be described in connection with the preferred embodiment described in the accompanying drawing.

An alternative to the above-described combination of mild acidic hydrolysis followed by caustic treatment is to carry out the acidic hydrolysis at considerably more severe conditions, e.g. at temperatures of 150 to 350° C. and sufficient pressure to maintain the liquid phase. At such conditions, faster ketal hydrolysis and partial ester hydrolysis can be accomplished in a single treatment. In addition, glycol ether impurities can be significantly reduced.

In order to more clearly describe the invention, reference is made to the accompanying drawing which illustrates a practice of the invention.

Referring to the drawing. the epoxidation reaction mixture formed as a result of the epoxidation of an olefin, preferably propylene, by reaction with a cycloalkyl hydroperoxide, is introduced via line 1 into distillation zone 2 wherein the light boiling materials, such as unreacted propylene, are removed overhead via line 3. The bottoms stream passes via line 4 to distillation zone 5 wherein a crude oxirane product, for example propylene oxide, is separated via line 6. The bottoms stream passes via line 7 to distillation zone 8 wherein the stabilizing material, preferably t-butyl alcohol, is separated overhead via line 9.

The bottoms stream from zone 8 comprises the valuable KA-Oil co-product of the process as well as certain impurities which are formed during the previous epoxidation and separation steps. It is this mixture which is treated in accordance with the present invention to recover improved quantities of the valuable KA-Oil components. The mixture passes via line 10 to hydrolysis zone 11 wherein the organic stream is contacted with at leas sufficient water, introduced via line 12, to saturate the organic solution. Most suitably, a substantial excess of water is employed sufficient to achieve an equilibrium reaction between ketal contained in the organic feed and product cycloalkanone and glycol. As above indicated, the conditions in hydrolysis zone 11 are maintained sufficient to accomplish the desired hydrolysis. The zone is maintained under acidic conditions, and mildly elevated temperatures and pressures are employed.

The mixture from zone 11, in a preferred embodiment, passes via line 13 to caustic treatment zone 14 wherein the organic stream is contacted with aqueous caustic at conditions effective to neutralize acids and to hydrolyze such esters as are contained in the organic mixture. An aqueous caustic phase is removed via line 15 and passed to steam stripping zone 16. Stripping steam is introduced by means of line 17, and an overhead comprised of steam and stripped organic materials passes via line 18 to distillation zone 19. An aqueous caustic stream is removed from zone 16 by means of line 20. The organic phase from caustic treatment zone 14 passes via line 21 to washing zone 22 wherein the organic materials are washed with water introduced via line 23 to remove traces of caustic. The aqueous stream passes from zone 22 via line 24 back to caustic treatment zone 14.

The washed KA-Oil mixture is removed from zone 22 and passes via line 25 to distillation zone 19. An overhead lights stream comprising water and some low boiling organic materials, including alcohols and ethers, are removed from zone 19 via line 26 condensed and decanted (not shown). The aqueous phase is recycled via lines 26A and 12 to provide acidic hydrolysis material to zone 11. A small amount of organics is purged. The KA-Oil stream is removed from zone 19 via line 27 and passes to distillation zone 28. A heavies product stream is removed via line 29, and the purified KA-Oil stream containing enhanced quantities of KA-Oil is separated by means of line 30.

Through practice of the present invention, substantially improved yields of KA-Oil are achieved.

EXAMPLE

An epoxidation reaction mixture resulting from the epoxidation of propylene with cyclohexyl hydroperoxide passes via line 1 to distillation zone 2. A $C_3$ hydrocarbon stream is separated overhead at 51° C. and 306 psia, and the bottoms stream passes via line 4 to distillation zone 5. An overhead crude propylene oxide product stream is separated via line 6 at 44° C. and 20 psia. The bottoms stream passes via line 7 to distillation zone 8 wherein t-butyl alcohol stabilizer is separated overhead via line 9 at 52° C. and 200 mm Hg.

The bottoms stream from zone 8 passes via line 10 to hydrolysis zone 11 wherein ketal is hydrolyzed to cyclohexanone and propylene glycol. Water is introduced into zone 11 via line 12 an hydrolysis conditions in zone 11 are 98° C. and 15 psia.

From zone 11 the hydrolysis mixture passes to caustic treatment zone 14 wherein the mixture is contacted with aqueous caustic at 105° C. and 15 psia. Caustic is introduced via line 31, and water is introduced via line 24 from washing zone 22.

An aqueous caustic phase is removed from zone 14 via line 15 and sent to steam stripping zone 16. Recovered KA oil and light organics are removed overhead at 99° C. and 760 mm Hg and pass to distillation zone 19. Caustic waster is separated via line 20 to an incinerator.

The organic phase from zone 14 passes via line 21 to water wash zone 22 wherein it is intimately contacted with water introduced via line 23 in a conventional countercurrent extraction apparatus. The aqueous phase passes via line 24 back to zone 14, and the washed organic phase passes via line 25 to distillation zone 19.

An overhead lights stream is separated via line 26 at 72° C. and 300 mm Hg, and this stream is condensed and decanted (not shown). The aqueous phase is separated and passed via lines 26A and 12 to hydrolysis zone 11.

Bottoms from zone 19 passes via line 27 to distillation zone 28. A KA-Oil product stream is separated overhead at 132° C. and 300 mm Hg via line 30. Heavies are removed via line 29.

The following table shows the quantities and compositions of the various streams at various points in the process based on an annual production of 185 million pounds per year of refined KA Oil.

TABLE 1

| KA OIL RECOVERY MATERIAL BALANCE, 185 MMLB/YR REFINED KA | | | | | | | | | | | | | |
|---|---|---|---|---|---|---|---|---|---|---|---|---|---|
| STREAM NO. | | 1 | | 3 | | 4 | | 6 | | 7 | | 9 | |
| COMPONENT | M.W. | lb/hr | wt % | lb/hr | wt % | lb/hr | wt % | lb/hr | wt % | lb/hr | wt % | lb/hr | wt % |
| Propylene | 42.08 | 128472.6 | 54.66 | 128446.9 | 100.00 | 25.7 | 0.02 | 25.7 | 0.22 | 0.0 | 0.00 | | 0.00 |
| PO | 58.08 | 11093.9 | 4.72 | | | 11093.9 | 10.41 | 11088.3 | 96.22 | 5.5 | 0.01 | 5.5 | 0.01 |
| TBA | 74.12 | 64471.3 | 27.43 | | | 64471.3 | 60.48 | 6.4 | 0.06 | 64464.9 | 67.81 | 64432.7 | 99.34 |
| Cyclohexanone | 98.14 | 3220.0 | 1.37 | | | 3050.3 | 2.86 | | | 2948.4 | 3.10 | 0.3 | 0.00 |
| Cyclhexanol | 100.16 | 19837.3 | 8.44 | | | 19837.3 | 18.61 | | | 19837.3 | 20.87 | | 0.00 |
| PG Ketal | 156.20 | 23.5 | 0.01 | | | 293.7 | 0.28 | | | 455.8 | 0.48 | | 0.00 |
| MPG | 76.10 | 329.1 | 0.14 | | | 197.4 | 0.19 | | | 188.5 | 0.12 | | 0.00 |
| Acids | 111.00 | 3243.5 | 1.38 | | | 3243.5 | 3.04 | | | 3243.5 | 3.41 | | 0.00 |
| Esters | 200.00 | 3173.0 | 1.35 | | | 3173.0 | 2.98 | | | 3173.0 | 3.34 | | 0.00 |
| KA Lights | | 188.0 | 0.08 | | | 188.0 | 0.18 | | | 188.0 | 0.20 | | |
| KA Heavies | | 188.0 | 0.08 | | | 188.0 | 0.18 | | | 188.0 | 0.20 | | |
| Water | 18.02 | 775.6 | 0.33 | | | 806.8 | 0.76 | 403.4 | 3.50 | 422.1 | 0.44 | 422.1 | 0.65 |
| NaOH | 40.00 | | | | | | | | | 0.0 | | | |
| Salts | | | | | | | | | | 0.0 | | | |
| Moly | 96.00 | 23.5 | 0.01 | | | 23.5 | 0.02 | | | 23.5 | 0.02 | | 0.00 |
| TOTAL | | 235039.5 | 100.00 | 128446.9 | 100.00 | 106592.6 | 100.00 | 11523.9 | 100.00 | 95068.7 | 100.00 | 64860.6 | 100.00 |

| STREAM NO. | | 10 | | 12 | | 13 | | 31 | | 24 | | 15 | |
|---|---|---|---|---|---|---|---|---|---|---|---|---|---|
| COMPONENT | M.W. | lb/hr | wt % | lb/hr | wt % | lb/hr | wt % | lb/hr | wt % | lb/hr | wt % | lb/hr | wt % |
| Propylene | 42.08 | 0.0 | 0.00 | | | 0.0 | 0.00 | | | 0.0 | 0.00 | 0.0 | 0.00 |
| PO | 58.08 | 0.0 | 0.00 | | | 0.0 | 0.00 | | | 0.0 | 0.00 | 0.0 | 0.00 |
| TBA | 74.12 | 32.2 | 0.11 | | | 40.2 | 0.10 | | | 7.7 | 0.10 | 9.6 | 0.05 |
| Cyclohexanone | 98.14 | 2887.0 | 9.56 | | | 3625.1 | 9.46 | | | 97.3 | 1.24 | 371.9 | 1.75 |
| Cyclhexanol | 100.16 | 19837.3 | 65.67 | | | 19837.3 | 51.74 | | | 567.6 | 7.22 | 1567.3 | 7.40 |
| PG Ketal | 156.20 | 553.1 | 1.83 | | | 110.6 | 0.29 | | | 5.5 | 0.07 | 5.8 | 0.03 |

TABLE 1-continued

KA OIL RECOVERY MATERIAL BALANCE. 185 MMLB/YR REFINED KA

| | | | | | | | | | | | | | |
|---|---|---|---|---|---|---|---|---|---|---|---|---|---|
| MPG | 76.10 | 71.1 | 0.24 | | | 286.6 | 0.75 | | | 54.6 | 0.69 | 273.0 | 1.29 |
| Acids | 111.00 | 3243.5 | 10.74 | | | 3243.5 | 8.46 | | | 0.0 | 0.00 | 0.0 | 0.00 |
| Esters | 200.00 | 3173.0 | 10.50 | | | 3173.0 | 8.28 | | | 1.5 | 0.02 | 1.6 | 0.01 |
| KA Lights | | 188.0 | 0.62 | | | 298.4 | 0.78 | | | 24.4 | 0.31 | 25.6 | 0.12 |
| KA Heavies | | 188.0 | 0.62 | | | 188.0 | 0.49 | | | 512.9 | 6.52 | 1025.8 | 4.84 |
| Water | 18.02 | 11.2 | 0.04 | 3359.3 | 100.00 | 7512.2 | 19.59 | 2164.1 | 50.00 | 5984.4 | 76.12 | 12146.6 | 57.31 |
| NaOH | 40.00 | 0.0 | 0.00 | | | 0.0 | 0.00 | 2164.1 | 50.00 | 38.5 | 0.49 | 364.7 | 1.72 |
| Salts | | 0.0 | 0.00 | | | 0.0 | 0.00 | | | 567.7 | 7.22 | 5378.3 | 25.38 |
| Moly | 96.00 | 23.5 | 0.08 | | | 23.5 | 0.06 | | | 0.0 | 0.00 | 23.5 | 0.11 |
| TOTAL | | 30208.1 | 100.00 | 3359.3 | 100.00 | 38338.6 | 100.00 | 4328.3 | 100.00 | 7862.1 | 100.00 | 21193.8 | 100.00 |

| STREAM NO. | | 21 | | 17 | | 18 | | 20 | | 23 | | 25 | |
|---|---|---|---|---|---|---|---|---|---|---|---|---|---|
| COMPONENT | M.W. | lb/hr | wt % | lb/hr | wt % | lb/hr | wt % | lb/hr | wt % | lb/hr | wt % | lb/hr | wt % |
| Propylene | 42.08 | 0.0 | 0.00 | | | 0.0 | 0.00 | 0.0 | 0.00 | | | 0.0 | 0.00 |
| PO | 58.08 | 0.0 | 0.00 | | | 0.0 | 0.00 | 0.0 | 0.00 | | | 0.0 | 0.00 |
| TBA | 74.12 | 38.3 | 0.13 | | | 9.4 | 0.40 | 0.2 | 0.00 | | | 30.7 | 0.11 |
| Cyclohexanone | 98.14 | 3350.4 | 11.42 | | | 364.5 | 15.65 | 7.4 | 0.03 | | | 3253.1 | 11.90 |
| Cyclhexanol | 100.16 | 19545.9 | 66.63 | | | 1536.0 | 65.95 | 31.3 | 0.13 | | | 18978.3 | 69.42 |
| PG Ketal | 156.20 | 110.3 | 0.38 | | | 5.7 | 0.24 | 0.1 | 0.00 | | | 104.8 | 0.38 |
| MPG | 76.10 | 68.2 | 0.23 | | | 0.0 | 0.00 | 273.0 | 1.17 | | | 13.6 | 0.05 |
| Acids | 111.00 | 0.0 | 0.00 | | | 0.0 | 0.00 | 0.0 | 0.00 | | | 0.0 | 0.00 |
| Esters | 200.00 | 30.2 | 0.10 | | | 1.6 | 0.07 | 0.0 | 0.00 | | | 28.7 | 0.10 |
| KA Lights | | 487.3 | 1.66 | | | 25.1 | 1.08 | 0.5 | 0.00 | | | 462.9 | 1.69 |
| KA Heavies | | 1025.8 | 3.50 | | | 51.3 | 2.20 | 974.5 | 4.17 | | | 512.9 | 1.88 |
| Water | 18.02 | 4040.5 | 13.77 | 4524.9 | 100.00 | 335.4 | 14.40 | 16336.1 | 69.84 | 5867.0 | 100.00 | 3923.2 | 14.35 |
| NaOH | 40.00 | 40.5 | 0.14 | | | 0.0 | 0.00 | 364.7 | 1.56 | | | 2.0 | 0.01 |
| Salts | | 597.6 | 2.04 | | | 0.0 | 0.00 | 5378.3 | 22.99 | | | 29.9 | 0.11 |
| Moly | 96.00 | 0.0 | 0.00 | | | 0.0 | 0.00 | 23.5 | 0.10 | | | 0.0 | 0.00 |
| TOTAL | | 29335.1 | 100.00 | 4524.9 | 100.00 | 2328.9 | 100.00 | 2328.9 | 100.00 | 5867.0 | 100.00 | 27340.1 | 100.00 |

| STREAM NO. | | 26 | | 26A | | 27 | | 29 | | 30 | |
|---|---|---|---|---|---|---|---|---|---|---|---|
| COMPONENT | M.W. | lb/hr | wt % | lb/hr | wt % | lb/hr | wt % | lb/hr | wt % | lb/hr | wt % |
| Propylene | 42.08 | 0.0 | 0.00 | 0.0 | 0.00 | 0.0 | 0.00 | 0.0 | 0.00 | 0.0 | 0.00 |
| PO | 58.08 | 0.0 | 0.00 | 0.0 | 0.00 | 0.0 | 0.00 | 0.0 | 0.00 | 0.0 | 0.00 |
| TBA | 74.12 | 32.0 | 10.80 | 8.0 | 0.17 | 0.0 | 0.00 | 0.0 | 0.00 | 0.0 | 0.00 |
| Cyclohexanone | 98.14 | 171.3 | 57.75 | 460.1 | 9.64 | 2986.2 | 12.14 | 0.0 | 0.00 | 2986.2 | 12.91 |
| Cyclhexanol | 100.16 | 0.0 | 0.00 | 0.0 | 0.00 | 20514.2 | 83.39 | 766.4 | 51.92 | 19747.8 | 85.40 |
| PG Ketal | 156.20 | 0.0 | 0.00 | 0.0 | 0.00 | 110.5 | 0.45 | 82.9 | 5.61 | 27.6 | 0.12 |
| MPG | 76.10 | 0.0 | 0.00 | 0.0 | 0.00 | 13.6 | 0.06 | 13.6 | 0.92 | 0.0 | 0.00 |
| Acids | 111.00 | 0.0 | 0.00 | 0.0 | 0.00 | 0.0 | 0.00 | 0.0 | 0.00 | 0.0 | 0.00 |
| Esters | 200.00 | 0.0 | 0.00 | 0.0 | 0.00 | 30.2 | 0.12 | 22.7 | 1.53 | 7.6 | 0.03 |
| KA Lights | | 48.8 | 16.45 | 110.3 | 2.31 | 328.9 | 1.34 | 0.0 | 0.00 | 328.9 | 1.42 |
| KA Heavies | | 0.0 | 0.00 | 0.0 | 0.00 | 564.2 | 2.29 | 558.6 | 37.84 | 5.6 | 0.02 |
| Water | 18.02 | 44.5 | 15.00 | 4192.8 | 87.88 | 21.3 | 0.09 | 0.0 | 0.00 | 21.3 | 0.09 |
| NaOH | 40.00 | 0.0 | 0.00 | 0.0 | 0.00 | 2.0 | 0.01 | 2.0 | 0.14 | 0.0 | 0.00 |
| Salts | | 0.0 | 0.00 | 0.0 | 0:00 | 29.9 | 0.12 | 29.9 | 2.02 | 0.0 | 0.00 |
| Moly | 96.00 | 0.0 | 0.00 | 0.0 | 0.00 | 0.0 | 0.00 | 0.0 | 0.00 | 0.0 | 0.00 |
| TOTAL | | 296.7 | 100.00 | 4771.2 | 100.00 | 24601.1 | 100.00 | 1476.1 | 100.00 | 23125.0 | 100.00 |

What is claimed is:

1. In a process for the preparation of an oxirane compound by catalytic epoxidation of a $C_2$ to $C_{20}$ alpha olefin with a cycloalkyl hydroperoxide formed by molecular oxygen oxidation of a $C_5$ to $C_{12}$ cycloalkane wherein a co-product mixture of cycloalkanol and cycloalkanone is produced, which also contains ketal impurity formed as a result of reaction between the cycloalkanone and glycol corresponding to the oxirane compound, the improvement which comprises reacting the mixture of cycloalkanol and cycloalkanone containing said ketal impurity with water at conditions effective to hydrolyze the said ketal.

2. The method of claim 1 wherein the olefinic compound is propylene.

3. The process of claim 1 wherein the cycloalkanol is cyclohexanol and the cycloalkanone is cyclohexanone.

* * * * *